(12) United States Patent
Rinner

(10) Patent No.: US 10,327,828 B2
(45) Date of Patent: Jun. 25, 2019

(54) MULTIPLE FULCRUM BENDER

(71) Applicant: Pacific Instruments, Inc., Honolulu, HI (US)

(72) Inventor: James A. Rinner, Franksville, WI (US)

( * ) Notice: Subject to any disclaimer, the term of this patent is extended or adjusted under 35 U.S.C. 154(b) by 278 days.

(21) Appl. No.: 15/234,226

(22) Filed: Aug. 11, 2016

(65) Prior Publication Data

US 2017/0042597 A1    Feb. 16, 2017

(51) Int. Cl.
*A61B 17/88*    (2006.01)

(52) U.S. Cl.
CPC ................ *A61B 17/8863* (2013.01)

(58) Field of Classification Search
CPC ............... A61B 17/88; A61B 17/8863
See application file for complete search history.

(56) References Cited

U.S. PATENT DOCUMENTS

2012/0047980 A1*  3/2012  Harper ............... B21D 7/063
                                                72/199
2014/0364860 A1* 12/2014  Knoepfle ........... A61B 17/8863
                                                606/101

* cited by examiner

*Primary Examiner* — Christopher Beccia
(74) *Attorney, Agent, or Firm* — Brainspark Associates, LLC

(57) ABSTRACT

A surgical bender for use in bending and/or plastically deforming a variety of types and/or shapes of materials in medical and/or surgical applications. Various embodiments include a compact and easily sterilizable multiple fulcrum arrangement that utilizes a series of interlocked actuating lever arms to greatly multiply an actuating force applied to a pair of handles for application to an intended material.

18 Claims, 14 Drawing Sheets

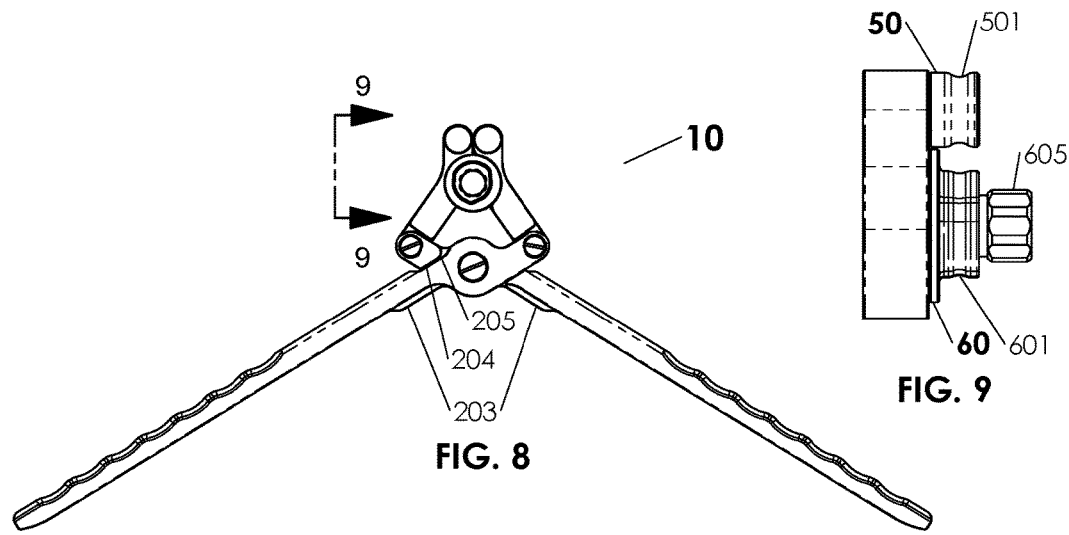
FIG. 8
FIG. 9
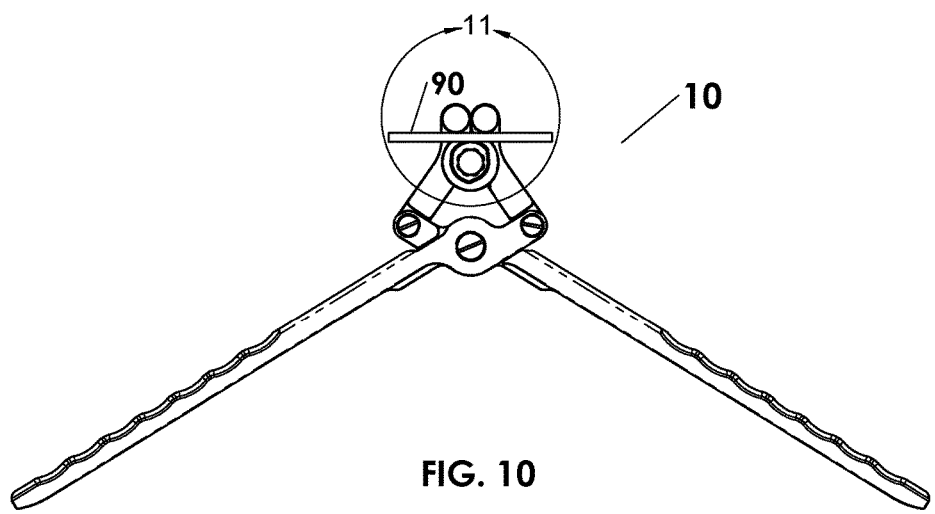
FIG. 10
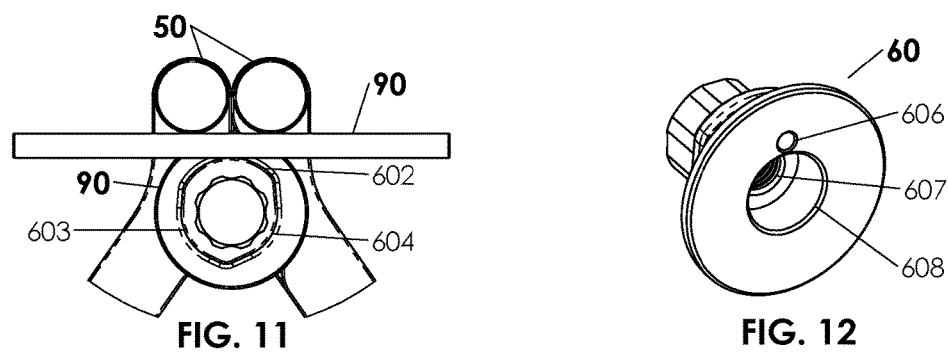
FIG. 11
FIG. 12

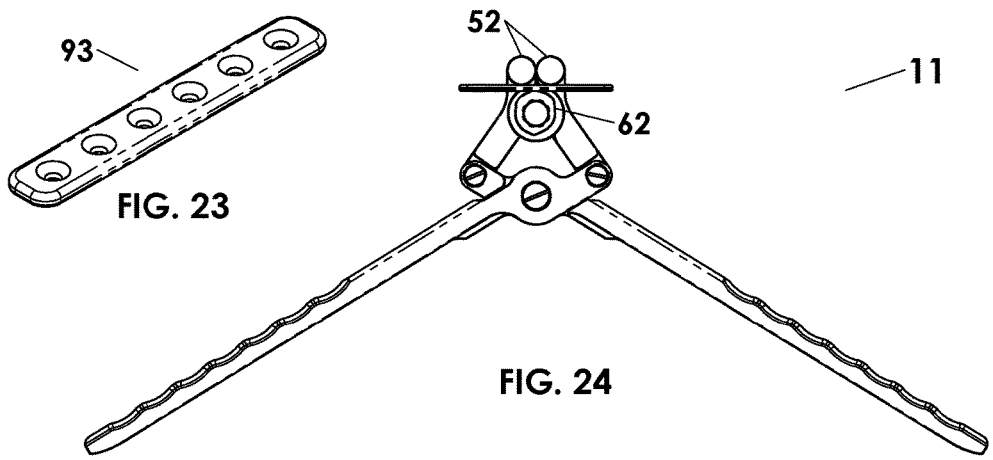
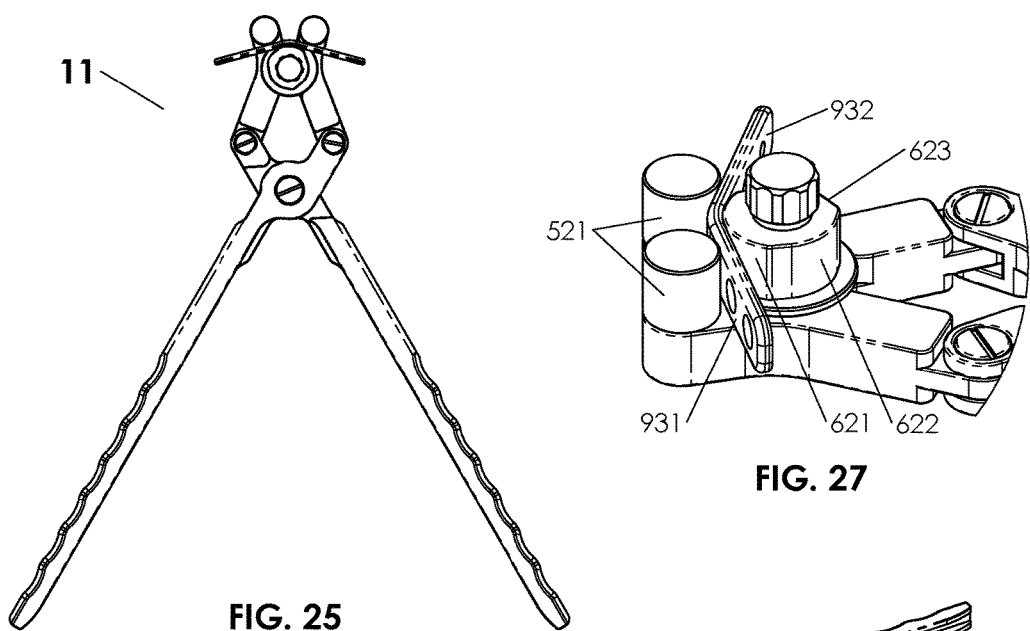
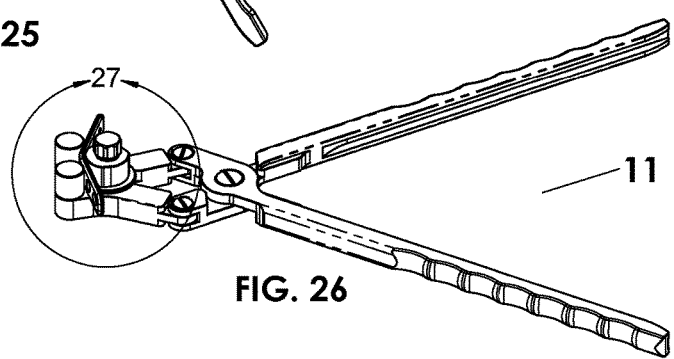

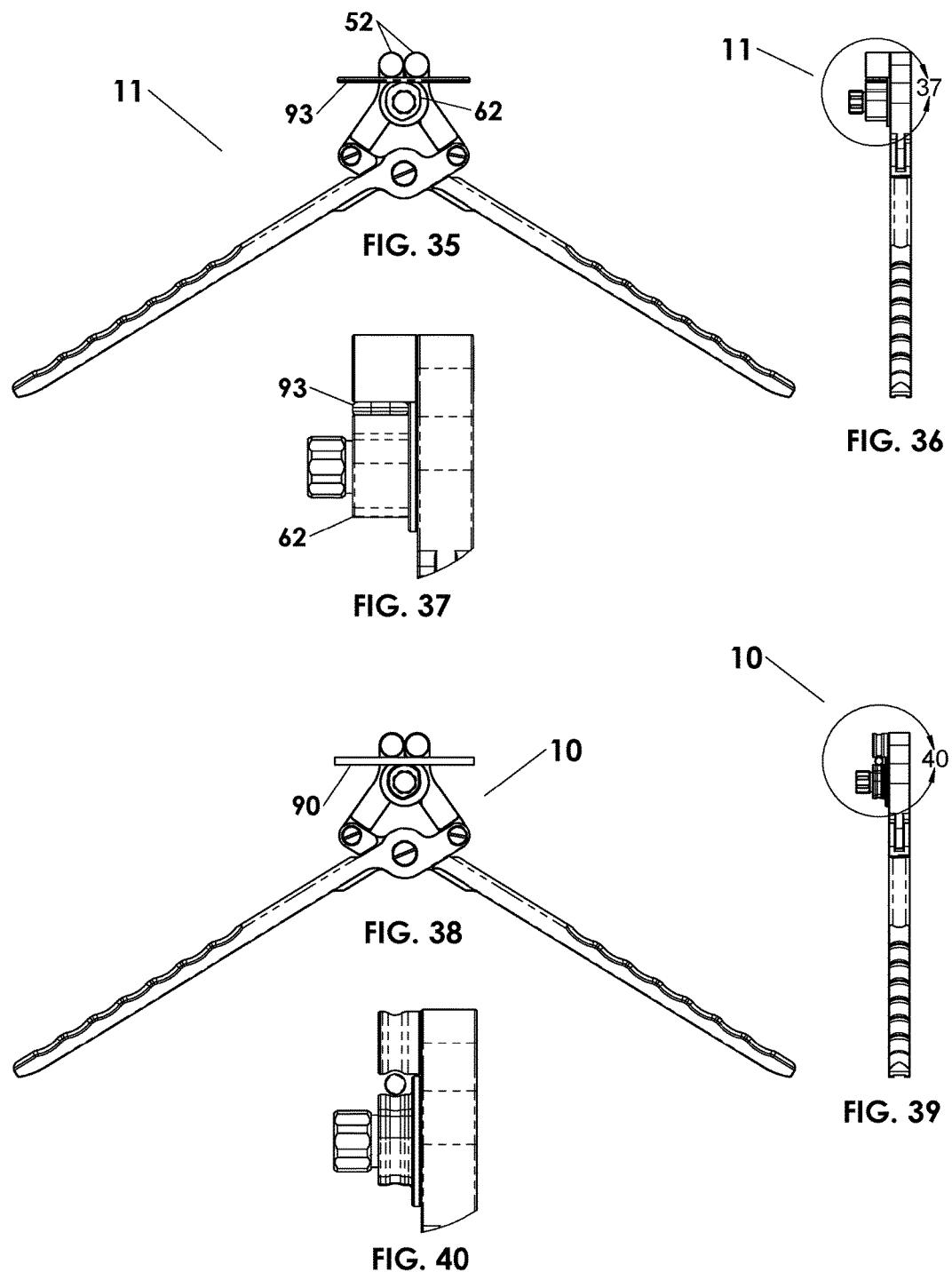

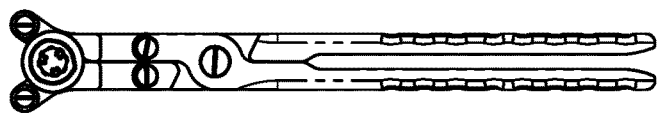
FIG. 53
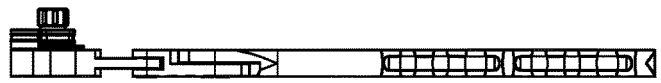 
FIG. 54                    FIG. 55
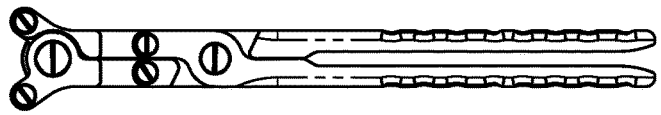
FIG. 56
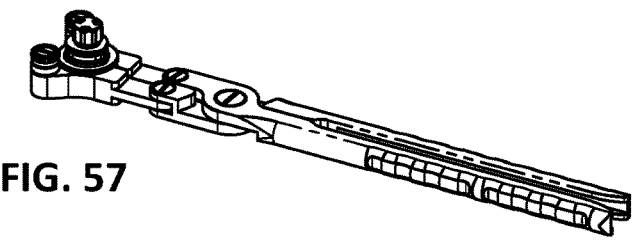
FIG. 57
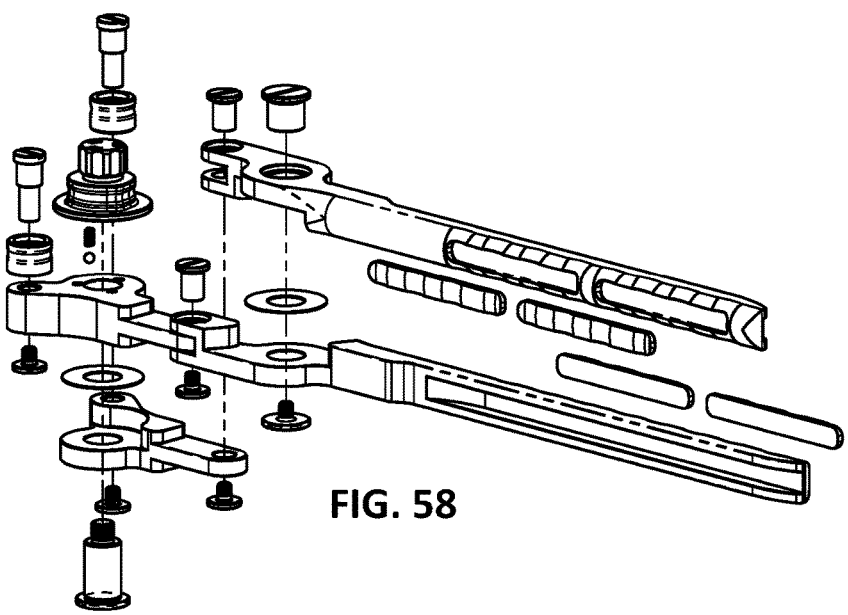
FIG. 58

MULTIPLE FULCRUM BENDER

CROSS-REFERENCE TO RELATED APPLICATIONS

This application claims the benefit of U.S. Provisional Patent Application Ser. No. 62/204,335 entitled "Multiple Fulcrum Bender," filed Aug. 12, 2015, the disclosure of which is incorporated by reference herein in its entirety.

TECHNICAL FIELD

Disclosed is a bending device and various components for use in a variety of fields, including in conforming orthopedic implants used in surgery.

BACKGROUND OF THE INVENTION

Anatomical support structures such as bones and related anatomy are susceptible to a variety of weaknesses that can affect their ability to provide support and structure. Weaknesses in such structures may have many causes, including degenerative diseases, tumors, fractures, and dislocations. Advances in medicine and engineering have provided surgeons with a wide variety of devices and techniques for alleviating or curing these weaknesses, including implantable devices such as intramedullary rods, fusion rods and surgical plates and associated hardware to temporarily or permanently repair damaged support structures and/or fuse together various bones (i.e., spinal stabilization and/or fusion procedures). However, such rods and/or plates will often need to be bent or modified to accommodate the unique and/or unusual anatomy presented by an individual patient.

Instruments used for bending surgical implants are known in the art, including tools for bending round surgical rods and/or flat plates made of titanium or stainless steel. Often, such benders will resemble tubes, pliers or slotted tools, or may be similar to a device such as a French Bender, where a plier type instrument is used to bend the implant, with the handles of the tool providing leverage for orbital rollers to form the rod or other material shape around a central radius. In many cases, the bending operation is done by hand, which may be very difficult if the surgical implant comprises a new type and/or design of implant, such as newer alloys of stronger and stiffer implant materials. In many cases, the amount of force and/or leverage needed to bend these new materials is much higher, and surgeons are having difficulty forming the implant. Therefore, there is a need for a new device design which allows a surgeon to easily and accurately bend spinal rods and/or plates prior to insertion in to the patient's anatomy.

SUMMARY OF THE INVENTION

The present invention, at its distal end has a mechanism that is similar to the French Bender design, but which incorporates an additional set of lever arms of unique design to greatly multiply and increase the amount of bending force applied to the implant. In various embodiments, the invention can be used to bend spinal rods, bone plates and/or other malleable products.

These and other objects, advantages, and features of the disclosure will be apparent from the following description, considered along with the accompanying drawings.

BRIEF DESCRIPTION OF THE DRAWINGS

The present invention will be more understood in the detailed description and the accompanying drawings.

FIG. 8 depicts a top planar view of the embodiment of FIG. 1, in a fully open position;

FIG. 9 is an enlarged partial side view of the area 9-9 shown in FIG. 8;

FIG. 10 depicts a top planar view of the embodiment of FIG. 1, in a fully open position, with one embodiment of a straight diametric rod in place;

FIG. 11 is an enlarged partial top view of the area 11 shown in FIG. 10;

FIG. 12 depicts a bottom perspective view of a cam component of the embodiment of FIG. 1;

FIG. 23 depicts a perspective view of one embodiment of a generic bone plate with planar surfaces;

FIG. 24 depicts a top planar view of another exemplary embodiment of a bender, shown in an open position;

FIG. 25 depicts a top planar view of the embodiment of FIG. 24, shown in a partially closed position;

FIG. 26 depicts a perspective view of the embodiment of FIG. 25;

FIG. 27 is an enlarged partial top view of the area 27 shown in FIG. 26;

FIGS. 35 and 36 depict top and side planar views of another exemplary embodiment of a bender, shown in an open position;

FIG. 37 is an enlarged partial side view of the area 37 shown in FIG. 36

FIGS. 38 and 39 depict top and side planar views of the bender of FIGS. 8 and 9, with an associated item to be bent;

FIG. 40 is an enlarged partial side view of the area 40 shown in FIG. 39;

FIGS. 53-57 depict various views of another exemplary embodiment of a double fulcrum bender;

FIG. 58 depicts an exploded perspective view of the embodiment of FIG. 53;

DETAILED DESCRIPTION OF THE DRAWINGS

In the following detailed description, for purposes of explanation, numerous specific details are set forth to provide a thorough understanding of the various embodiments of the disclosure. Those of ordinary skill in the art will realize that these various embodiments are illustrative only and are not intended to be limiting in any way. In addition, for clarity purposes, not all of the routine features of the embodiments described herein may be shown or described for every alternative embodiment. One of ordinary skill in the art would readily appreciate that in the development of any such actual implementation, numerous implementation-specific decisions may be required to achieve specific design objectives. These design objectives may vary from one implementation to another and from one developer to another, and the variations and embodiments thereof are contemplated and included in the present disclosure.

Function

The intended use of the various embodiments of the bender(s) described herein are intended for handheld, unpowered use, but it should be understood that the various mechanical functions could also be used in an installed (i.e., permanent) device and/or in a device powered by electricity, gears, pneumatic and/or hydraulic power.

Components

Those of ordinary skill in the art should realize that the various embodiments described herein are illustrative only, are not intended to be limiting in any way and can be combined and subtracted to fit the specific needs of various designs of benders.

Desirably, the overall dimensions and/or thickness or width of the bender (as well as the remaining components of the bender) can be customized or particularized to an individual item that requires bending, straightening and/or other manipulation.

Figure 1:
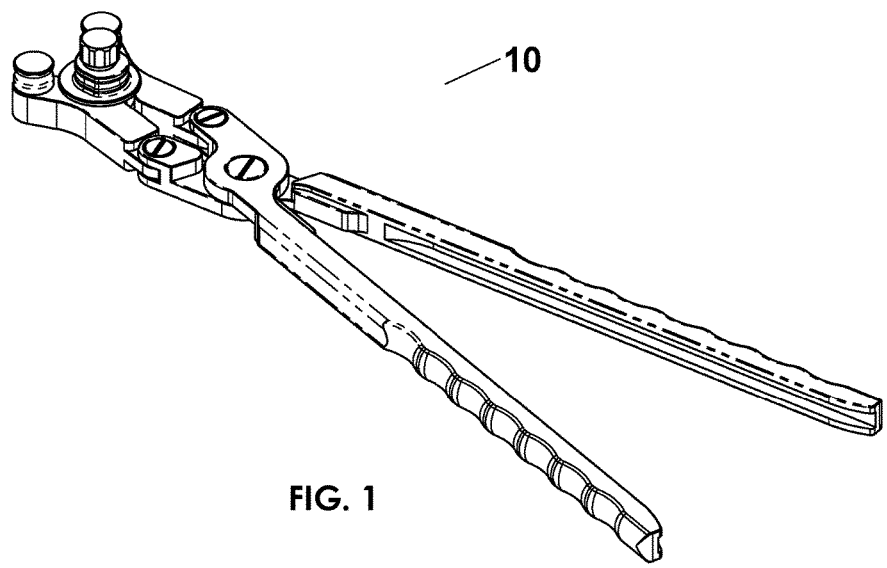
FIG. 1 depicts a perspective view of one exemplary embodiment of a bender, in a semi-open position for bending diametric rods.

FIG. 1 depicts a perspective view of one exemplary embodiment of a bender 10. In the figure, the bender 10 is shown in a partially open position to demonstrate the various arrangements of the pivoting joints.

Figure 2:
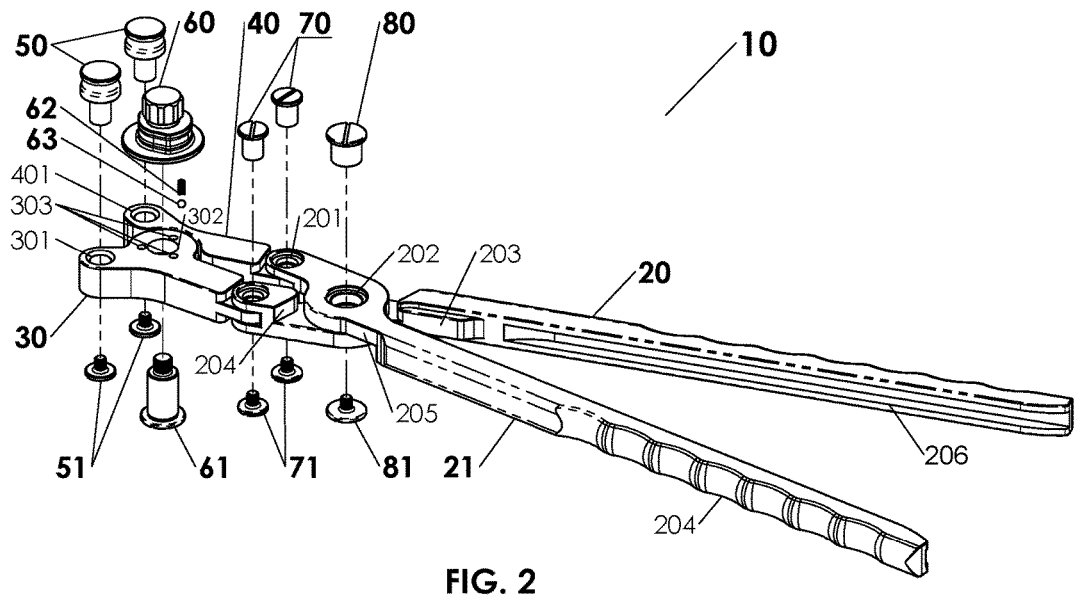
FIG. 2 depicts an exploded perspective view of the embodiment of FIG. 1.
Figure 3:
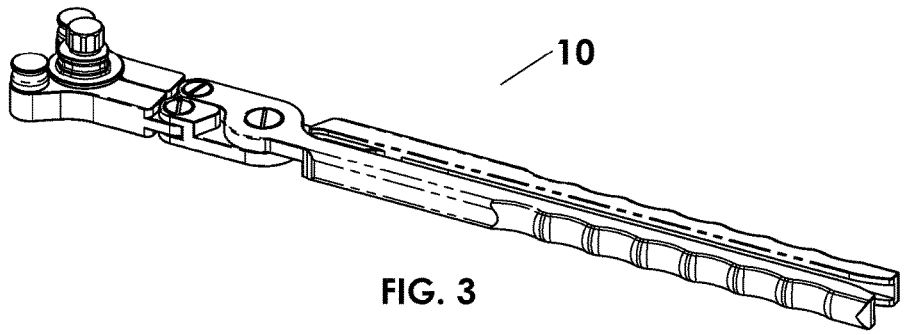
FIG. 3 depicts a perspective view of the embodiment of FIG. 1 in a fully closed position.

FIG. 2 depicts an exploded perspective view of the bender 10 showing a plurality of arms 20, 21, 30 and 40. A first set of arms 20 and 21 are shown as identical or "mirror-image" components in the present embodiment, but those of ordinary skill should realize that the two arms could contain features that make them unique without limiting the intent of the invention. However, the use of mirror image components can significantly reduce manufacturing costs in many embodiments, if desired.

Figure 4:
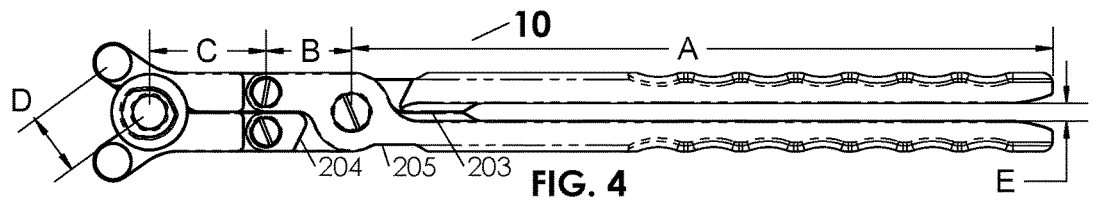
FIG. 4 depicts a top planar view of the embodiment of FIG. 3.
Figure 5:
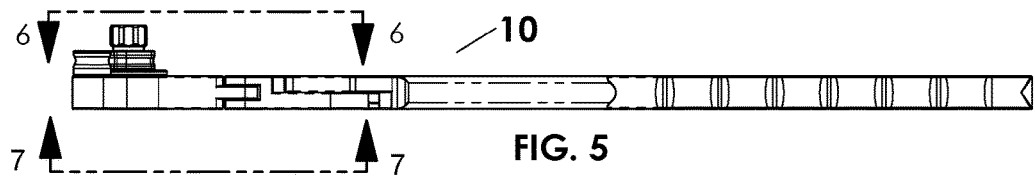
FIG. 5 depicts a left side planar view of the embodiment of FIG. 3.

Arms 20 and 21 are pivotally joined in the pivot diameter 202, and incorporate travel limiting surface features 203 that desirably stop the pivoting movement of the handles coming together when the surfaces 203 contact each other (SEE FIG. 4) in a closing direction. In an opening direction, the surfaces 204 and 205 desirably stop the pivoting movement of the arms at a maximum opening distance, when the surface 204 of one arm contacts the surface 205 of the other arm (see FIG. 8). Those skilled in the art should understand that various other surface arrangements can be used to stop, limit and/or control the open and/or closing motions besides those surfaces and surface arrangements previously referenced. The arms 20 and 21 are pivotally secured with a post 80 and a post screw 81. The attachment of the arms at pivot diameter 202 creates a fulcrum between two lengths (A and B) of the lever arms, as seen in FIG. 4. Since length A is longer than length B, this lever arrangement causes the force applied to the longer length A to be multiplied at the end of length B. Also shown in the first set of arms 20 and 21 (SEE FIG. 2) are the lightening grooves 206, which can be incorporated to reduce the weight of the arms, and the scallops 204 to provide a secure grip on the arms for a user.

Also shown in FIG. 2 is the second set of arms 30 and 40, which are pivotally connected to each other at diameter 302 by the cam 60 and cam post 61. The male diameter and thread on cam post 61 desirably mate with the female diameter 608 and thread 607 of the cam 60 (SEE FIG. 12). This creates a second set of lever arms C and D, having a fulcrum at diameter 302 (SEE FIG. 2) where Length C is longer than length D (See FIG. 4) creating an additional multiplier of force at the cam followers 50. Also seen in FIG. 2 are the selector spring 62 and selector ball 63. Prior to the assembly of the cam 60 onto the cam post 61, the selector spring 62 can be placed into the hole 606 of cam 60 (SEE FIG. 12), with the selector ball 63 placed between the selector spring 62 and the arm 30. The selector spring 62 desirably applies force to the selector ball 63 to maintain the selector ball 63 in contact with the arm 30, thereby providing a positive stop and/or friction fit to keep the cam 60 from freely spinning relative to the arm 30. Also circumferentially located on the arm 30 are conically shaped selector dimples 303, which are configured and sized to accommodate a portion of the selector ball 63, which can "drop" into the dimples 303 in a known detent ball-type arrangement, providing a positive positional stop, or location, for the cam 60. The conical edge shape of the dimples 303 desirably allow the selector ball 63 to compress the selector spring 62 and move outward of the dimples 303, when rotation of the cam 60 is desired, which can then be rotated to another desired position. This movement will be further described later. Attached to the second set of arms are the bending rollers 50, which are attached through diameters 301 and 401 of arms 30 and 40, respectively. To secure the bending rollers 50, a bending roller screw 51 can be used.

The second set of arms 30 and 40 are desirably attached to the first of arms 20 and 21 by attachment pivot posts 70 and attachment pivot screws 71. This arrangement creates two sets of lever arms, A and B plus C and D, that are pivotally attached through the locations defined by the attachment pivot posts 70. This arrangement creates an additional multiplier of force acting at a distal end of lever arm length D for the force that is applied at or near a proximal end of lever arm length A. The table below demonstrates one exemplary multiplier of force arrangement as provided by various designs here:

| A:B length ratio | C:D length ratio | Applied force at A | Pivot Post Force | Resulting force at D |
|---|---|---|---|---|
| 10:1 | 2:1 | 20 lbs. | 200 lbs. | 400 lbs. |

Various embodiments of the present invention incorporate the use of a multiple fulcrum arrangement to greatly increase the bender's mechanical advantage, without significantly increasing its size and/or weight. The introduction of additional lever arms and associated pivot points can increase the device's output force markedly, potentially reducing the applied force (from the surgeon) required to contour a surgical rod (when compared to a traditional bender) and/or enabling the surgeon to easily and conveniently bend larger rods and/or other items as well as those incorporating newer, high strength materials. The relationship between the sets of lever arms can be correlated to the instrument's output force(s), with the employment of a multiple fulcrum arrangement in the various disclosed embodiments greatly increasing the resulting bending force.

The above table demonstrates that, if length A was 10 times longer than length B, and length C was 2 times longer than length D, then a 20 pound applied force at the proximal end of arms 20 and 21 would result in a force at the attachment pivot posts 70 of 200 pounds (10×20), and a final applied force at the bending rollers of approximately 400 pounds (2×200).

In various alternative embodiments, a wide variety of lever arm lengths, shapes and/or sizes are contemplated herein. In at least one exemplary embodiment, the length of lever arm A is 12.5 cm, the length of lever arm B is 1.5 cm, the length of lever arm C is 2.1 cm and the length of lever arm D is 1.1 cm. In at least a first desirable arrangement, the length of the various lever arms could comprise: A>B=C>D. In a second desirable arrangement, the length of the various lever arms could comprise: A>B>C>D. In a third desired arrangement, the length of the various lever arms could comprise: A>B<C>D.

If desired, the second set of arms (i.e., arm C/D) could comprise thicker and/or stronger materials and/or shapes than the first set of arms (i.e., arm A/B), enabling these arms to resist the greater applied forces transferred therein without significantly increasing the overall weight of the device. In a similar manner, some portions and/or all of the first set of arms could be made lighter (i.e., especially along locations where the lowest forces are applied, such as along the proximal portions of the user handles) without unduly sacrificing strength and/or durability of the entire instrument.

If desired, an additional fulcrum (i.e., a third or more set of additional pivoting arms) could be added to various embodiments, such as to the disclosed second set of arms (or modified arms, if desired), to further increase the resulting bending force. This additional fulcrum could comprise a permanent component and/or attachment to the bending device, or optionally could comprise a modular and/or removable attachment to a bender.

FIGS. 60-64 depict one exemplary embodiment of a modular fulcrum augment 1100 which can optionally be added to various bending devices to significantly increase the precision and/bending strength of the bender to which it is attached. The augment 1100 includes a pair of pivoting arms 1110 and 1120, connected by a pivot 1130 (which can incorporate a rotatable cam with differing circumferential bending surfaces), with a pair of pivoting rollers 1150 and 1160 positioned proximate to the distal ends of the arms 1110 and 1120. A pair of engagement cups 1170 and 1180 are provided at proximal ends of the arms 1110 and 1120, with the engagement cups desirably sized and/or configured to engage rollers (or other structures) on the distal ends of the bender.

Figure 65:
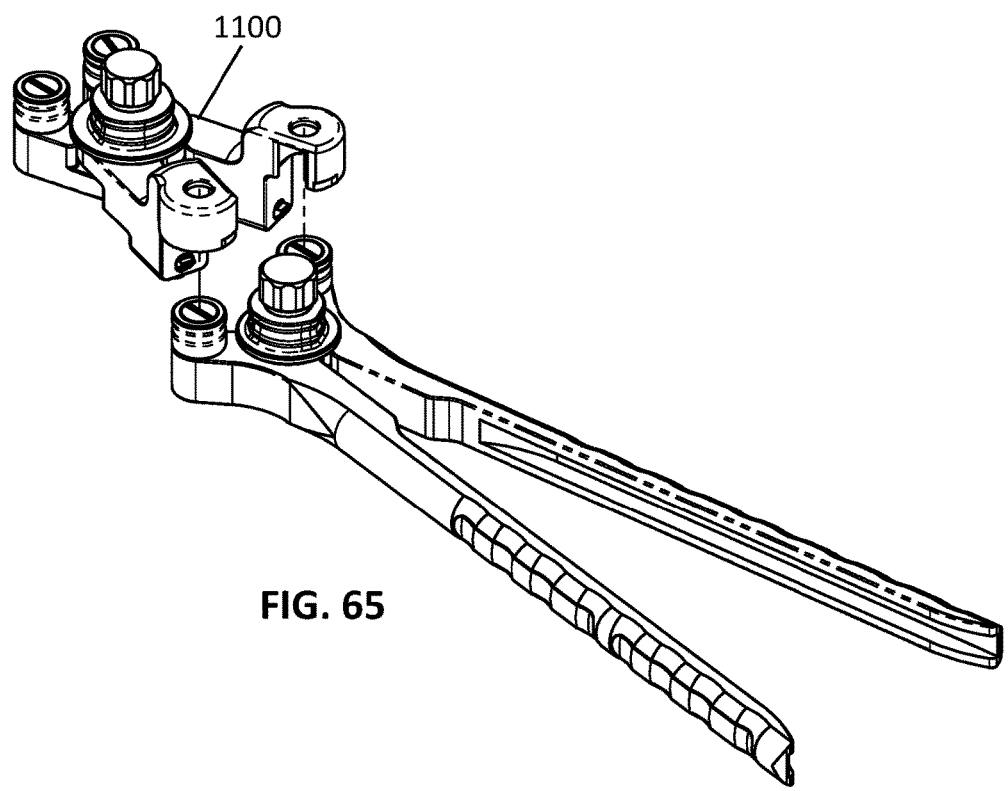
FIG. 65 depicts an exploded perspective view of the modular fulcrum augment of FIG. 60 being attached to the single fulcrum bender of FIG. 59.
Figure 66:
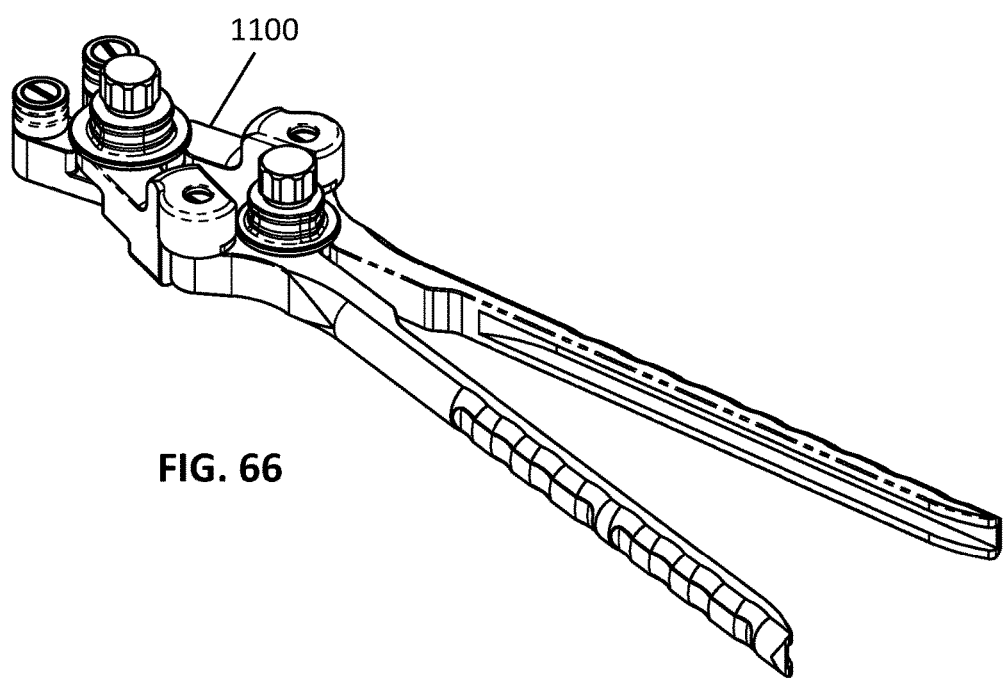
FIG. 66 depicts a perspective view of the modular fulcrum augment of FIG. 60 mounted to the single fulcrum bender of FIG. 59.
Figure 67:
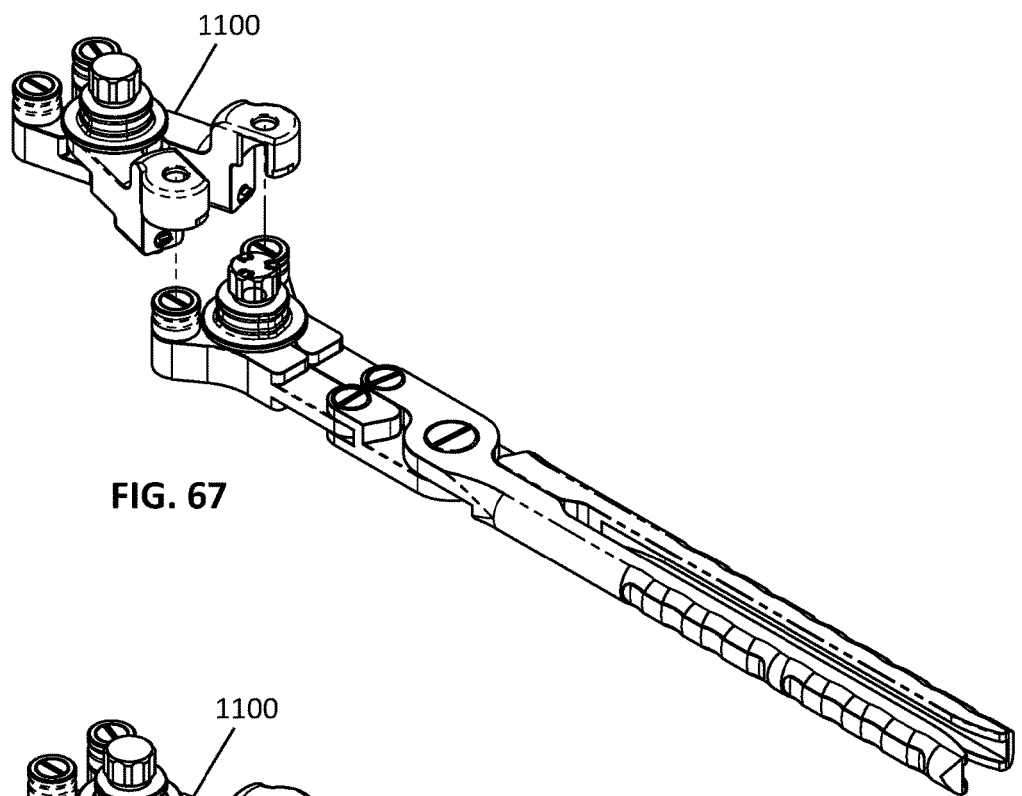
FIG. 67 depicts an exploded perspective view of the modular fulcrum augment of FIG. 60 being attached to the double fulcrum bender of FIG. 53.
Figure 68:
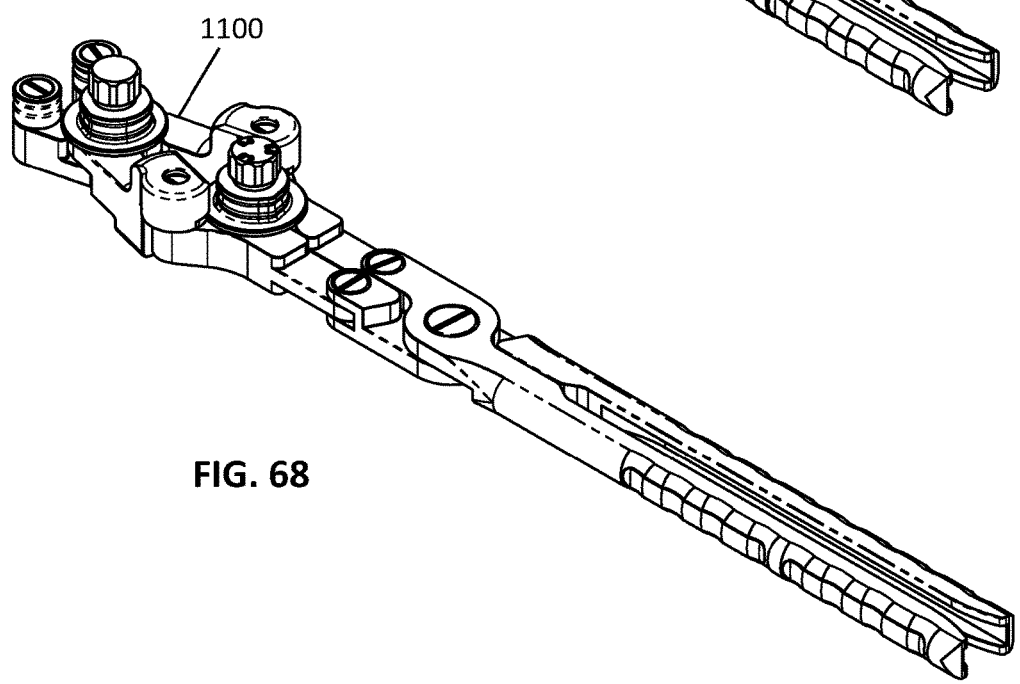
FIG. 68 depicts a perspective view of the modular fulcrum augment of FIG. 60 mounted to the double fulcrum bender of FIG. 53.

In use, the augment 1100 can be attached to a suitable bender, which in the disclosed embodiment of FIGS. 65 and 66 is a single fulcrum bender 1200, and in the disclosed embodiment of FIGS. 67 and 68 is a dual fulcrum bender 1300. Desirably, the inner surfaces of the cups 1170 and 1180 can be sized and configured to accommodate the rollers of the benders 1200 and 1300, which could include a friction fit and/or slide fit between the cups and the rollers, or the cups could retain the rollers using clamps, screws, clips, detents, locks, adhesives and the like. If desired, the cups could include internal surface features that engage with corresponding external surface features on the rollers and/or cam, such as complimentary concave/convex and/or expanding/contracting surfaces. Alternatively, various other connection arrangements for the augment 1100 could be provided to accommodate various connection points to the bender embodiments disclosed herein, as well as attachment to currently-existing bending tools that may be available from various instrument manufacturers. In various alternative embodiments, the augment 1100 could connect to a bender using clamps or engagement pins or the like, including engagement to the pivoting arms, rollers and/or cam of an existing bender, as well as to underlying features and/or locations on the bender arms (or other structures) that may be available for connection if component pieces such as the rollers and/or cam are removed from the bender.

If desired, various embodiments of an augment can be provided that incorporate one, two, three or more fulcrum points. If desired, a plurality of augments could be attached to a single bending instrument, including in a multi-augment "daisy-chain" fashion. In various alternative embodiments, a kit containing a plurality of single fulcrum augments could be provided, with each augment including different surfaces for accommodating different shaped items to be bent, wherein a surgeon could attach and detach different augments to a single bender to bend different items and/or to bend a single item in a plurality of ways. If desired, an augment could magnify the force exerted by the bender, or could alternatively lessen or reduce the force exerted by the bender, if desired.

If desired, the augment could be permanently attached to a bender, or it could be removable and/or modular.

In addition to force multiplication, the range of movement of such additional arms or augment (and the associated degree of bending accomplished on an item) could be significantly less than the amount of movement input by the physician (i.e., the movement applied to the handles), which in various embodiments could provide a very precise, carefully controlled amount of bending with significant bending force. This could be quite advantageous for small, precise bending of an item, including bending of extremely strong items. If desired, the third set of arms could be modular and/or removable from the bender, or could be permanently attached. In various embodiments, the removable set of arms could attach to a distal end of a second set of arms, or could attach directly to the rollers of a bender.

In various embodiments, a kit containing a plurality of additional modular arms of differing sizes and/or shapes could be provided, with each modular arm configured for attachment to an existing bending device, such as a French Bender-type device (as well as to various combinations of the embodiments described herein), wherein each of the modular arms incorporates one or more elements having a differing size and/or shape from those of corresponding modular arms in the kit. Desirably, each modular arm could include features that desirably provide a differing type of bending or bending surface(s) (for example, for bending different shapes and/or sizes of items), a different amount of bending (i.e., differing amount and/or types of bending movements, including compound movements) and/or a differing degree of mechanical advantage to the bending action, wherein a surgeon could utilize one or more differing modular arm attachments to accomplish a desired multi-stage bending operation.

Those skilled in the art should understand that a wide variety of component types and arrangements could be utilized to retain the various mating components described herein, in addition to the described screws 51, 61, 71 and 81. Such other methods could include, but are not limited to, press fits, welding, rivets and clips.

FIGS. 3-7 depict various views of the bender 10 in a fully closed position, where the distance between the bending rollers 50 is at a greatest extent. In the top view of FIG. 4, a gap E is shown that desirably provides a sufficient gap to avoid a "pinch point" between the arms 20 and 21, thus protecting the surgeon's hands (and sterile gloves, etc.) from a potential injury or damage. For example, if the item to be bent failed suddenly during a bending operation, the compression forces being exerted by the surgeon (and lack of resistive forces from the item being bent) might allow the handles 20 and 21 to close together very quickly, which could pinch and injure the surgeon between the handles 20 and 21 (in absence of the predesigned handle gap E). Similarly, if some portion of the bending rod mechanism should fail during a bending operation, the gap E would similarly protect the surgeon from inadvertent injury.

Figure 6:
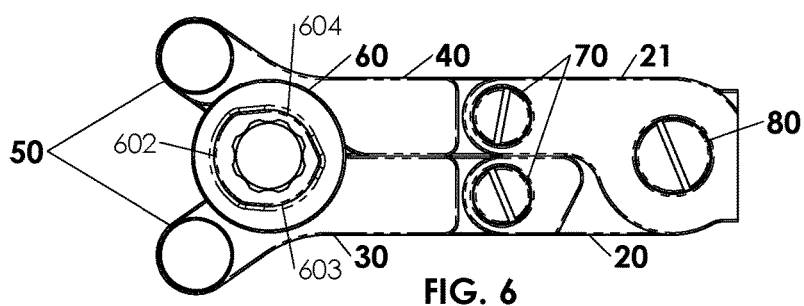
FIG. 6 is an enlarged partial top view of the area 6-6 shown in FIG. 5.

FIG. 6 depicts one exemplary embodiment of a multiple-action cam 60, which includes a plurality of cam surfaces 602, 603 and 604 having different surface shapes and/or radii. These different cam surfaces desirably allow a surgeon to alter the cam surface facing towards the item to be bent, and different surface arrangements can accommodate different types of items (i.e., round or flat rods, as well as items having convex/concave and/or complex surface features). Similarly, the differing radii of the cam surfaces 602, 603 and 604 can alter the spacing between the cam 60 and the rollers 50 (to accommodate items of greater or lesser diameters or thicknesses placed between the bending rollers 50 and cam 60), and various arrangements can also alter the amount of force multiplication provided to the distal tip of the bender, if desired. Each cam surface can include a variety of bending surface contours, which in various embodiments can enable the bender to accommodate different size and/or shape items, as well as provides for varying severities or contours of bending to be applied to the item.

In the various embodiments described herein, the cam 60 will desirably rotate around cam post 61, which as disclosed is fixed into diameter 302, but which in various embodiments desirably does not translate (i.e., lift off) relative to either arm 30 or arm 40.

Figure 7:
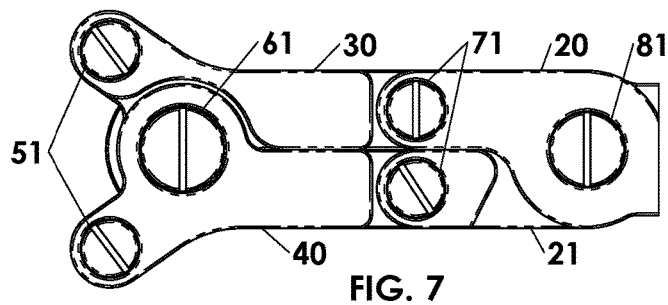
FIG. 7 is an enlarged partial bottom view of the area 7-7 shown in FIG. 5.
Figure 13:
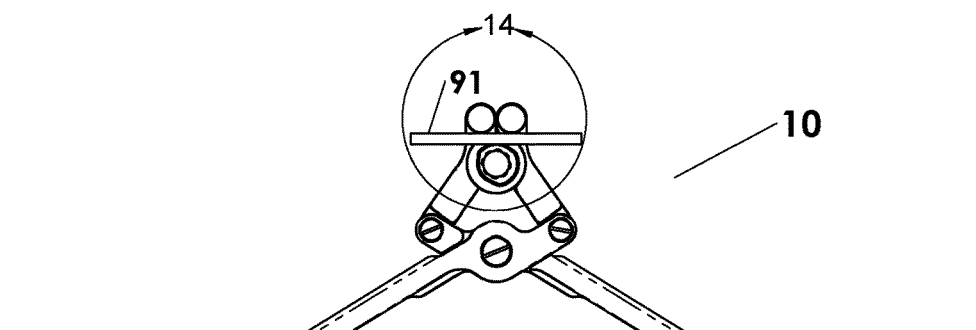
FIGS. 13 and 15 depicts top planar views of the embodiment of FIG. 1, in a fully open position, with a straight diametric rod in place, the straight rod in FIG. 13 being of greater diameter than the rod shown in FIG. 10 and the straight rod in FIG. 15 being of greater diameter than the rod shown in FIG. 13.
Figure 14:
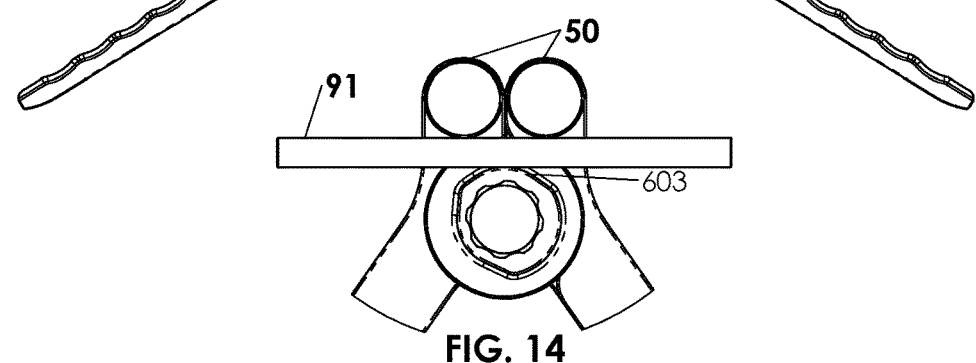
FIGS. 14 and 16 are enlarged partial top views of the areas 14 and 16 of FIGS. 13 and 15.
Figure 15:
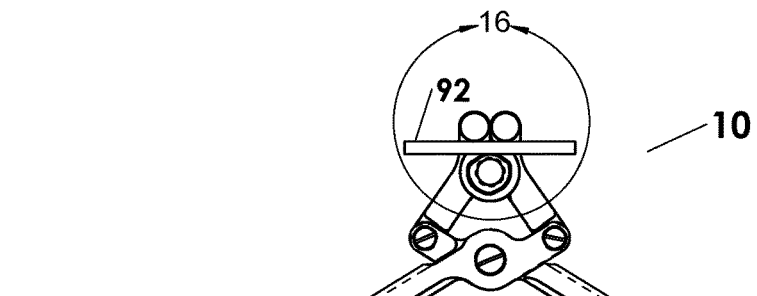
Figure 16:
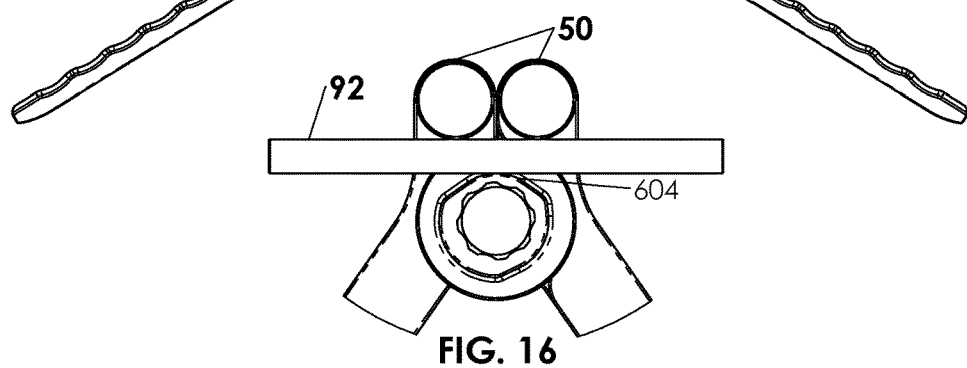
Figure 17:
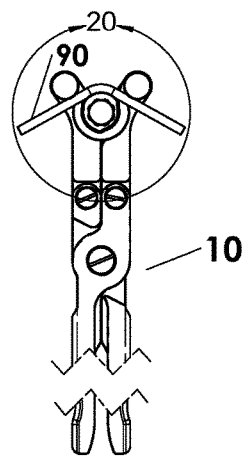
FIGS. 17-19 depict top planar broken views of the embodiment of FIG. 1 in the fully closed position, with bent diametric rods in place that are of different diameters.
Figure 18:
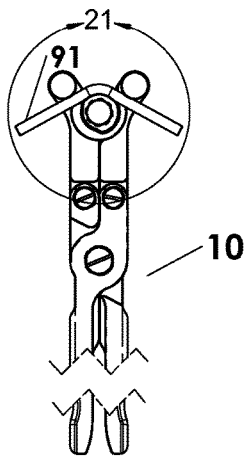
Figure 19:
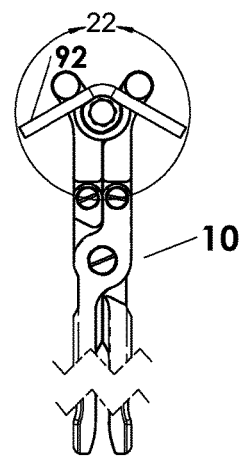
Figure 20:
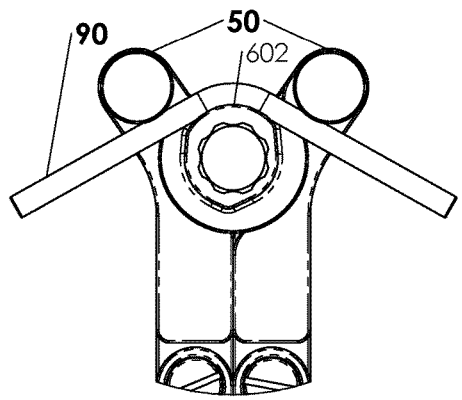
FIGS. 20-22 are enlarged partial top views of the areas 20, 21 and 22 shown in FIGS. 17-19.
Figure 21:
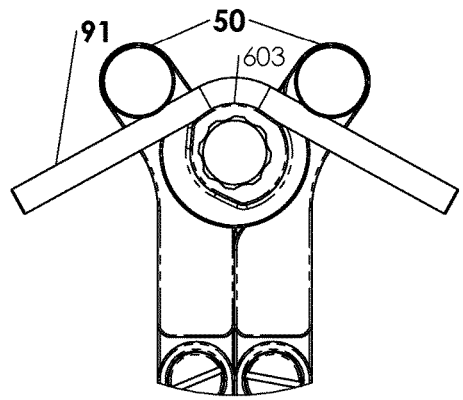
Figure 22:
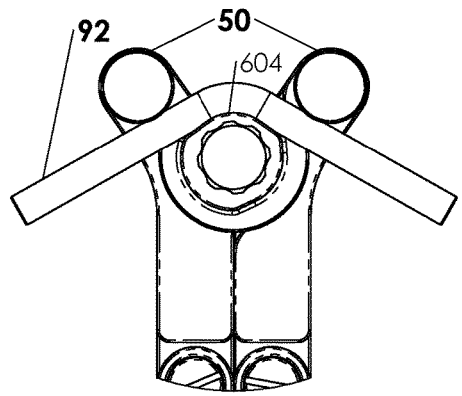
Figure 28:
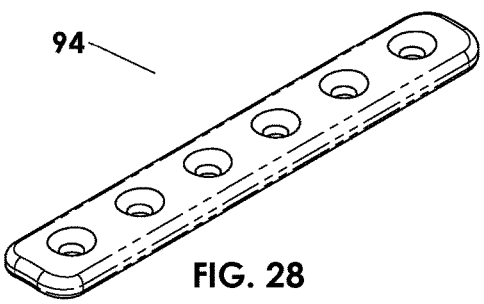
FIG. 28 depicts a perspective view of a generic bone plate, showing concave and convex surfaces.
Figure 29:
FIG. 29 depicts a side view of the plate of FIG. 28.

FIG. 7 depicts various screws 51, 71, 81 and cam pivot post 61, which are used to secure the pivoting components 50, 70, 80 and 60, respectively.

FIG. 8 depicts the bender embodiment 10 in a fully "open" position, where surfaces 204 and 205 can come in contact with each other (if desired) to limit outward motion of the arms 20 and 21. In this position, the bender 10 will desirably provide an enlarged opening or gap to accommodate the item to be bent (i.e., the spacing between the cam 60 and a line drawn between the rollers 50 will desirably be at a larger separation distance as shown in FIG. 40).

FIG. 9. Is an enlarged view from area 9-9 of FIG. 8, and depicts a cam knob 605, which can be used to rotate the cam 60, and a cam radial groove 601, which in this embodiment can follow the contour of the cam surfaces 602, 603 and 604. Also shown in FIG. 9 is a bending roller radial diameter 501, which in this embodiment is a concave surface that extends around the entire periphery of the cam roller. The cam and bending radii are useful in securing, holding and bending of an implant rod 90 (SEE FIGS. 10 and 11), and also desirably help in reducing the occurrence of marks, indentations or other surface blemishes being imprinted into the item being bent during the bending procedure. Those of ordinary skill should appreciate that, depending on the item being bent, the outer surface of the radii could be exchanged for flat-bottomed surfaces, multiple radii surfaces, textured surfaces, convex/concave surfaces (or various combinations thereof) and/or rollers having no grooves or surface texturing all together.

FIGS. 10, 11 and 38 through 40 depict the bender 10 in a fully open position, with a round implant rod set between bending rollers 50 and the cam 60. FIG. 11 is an enlarged view of area 11 from FIG. 10, and shows the three cam surfaces 602, 603 and 604, in which cam surface 602 is facing towards the rollers 50. In this arrangement, the cam surface 602 (which has the greatest radii on the cam 60, in this embodiment) and rollers 500 will desirably accommodate smaller items, such as a smaller diameter implant rod 90, while also allowing larger diameters items to be bent. For different sizes and/or shapes of items to be bent, the item can be placed between the cam 60 and the rollers 50, and the cam 60 subsequently rotated until one or more of the cam surfaces 602, 603 or 604 is directly adjacent to the rod 90. When turning the cam 60, the selector spring 62 desirably urges the selector ball 63 to travel into and/or out of the selector dimples (i.e., a detent feature), and when the cam 60 reaches a desired orientation, the selector ball 63 can drop into the one of the selector dimples—which then holds the cam 60 in the proper position. In alternative embodiments, the cam could incorporate frictional retaining features such as a thrust washer (not shown) to resist unwanted cam motion and/or maintain the cam in a desired position. In other alternative embodiments, the cam may be allowed to rotate freely, with frictional rotation resistance induced by a bending operation that desirably maintains the cam in a specific orientation.

As the rod diameter of an intended item to be bent increases (SEE FIGS. 13-16), the cam can be rotated to an alternate position in order to accommodate the placement of the larger rods 91 and 92, with cam radii surfaces 603 and 604 respectively. Those of ordinary skill should understand that the cam 60 can be one single diameter, or two or three or more cam radii surfaces can be incorporated into a single cam 60, depending on the implant system and bent items with which the bender is being used. Also, those with ordinary skill should understand that, in many situations, an implant rod 90 could be bent using multiple sides of such cam radii positions, if desired.

FIGS. 17-22 demonstrate how the bender 10 of the present invention could be employed to form, or bend, a rod or other item to a desired shape when the item is placed between the rollers and cam and the arms 20 and 21 of the bender 10 are brought together. When the arms 20 and 21 are brought together, the bending rollers 50 desirably move in an arcuate motion, forming the rod around the chosen cam surface. The enlarged area views 20, 21 and 22 show the various rod diameters 90, 91 and 92, along with respective cam surfaces 602, 603 and 604.

FIG. 23 is a perspective view of a generic bone plate 93. Those skilled in the art should appreciate that bone plates can be provided in various lengths, widths and/or shapes, including flat (as shown) or with various curvatures, surface texturing, radii and/or appendages. The depicted generic bone plate 93 is used to show various features and functions of another alternative embodiment of a bender 11, when used to bend a plate or similar item.

FIGS. 24-26 depict a bender 11 which is used to bend a bone plate 93. Similar to the embodiment of the FIG. 10, this depicted bender can be used to bend the implant by bringing the proximal arms together. However, in this embodiment the bending rollers 52 will desirably incorporate smoother, flattened surfaces 521, with the cam 62 having similar flat radial surfaces 621, 622 and 623 (SEE FIG. 27). Similar to the rod diameter increasing in (SEE FIGS. 13-16), the cam 62 can be rotated to an alternate position in order to accommodate the placement of the thicker plates with cam surfaces 622 and 623 respectively.

Figure 30:
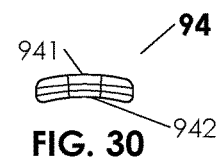
FIG. 30 depicts an end view of the plate of FIG. 28.
Figure 31:
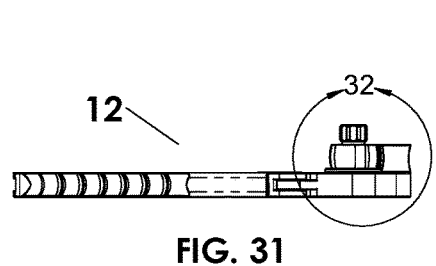
FIG. 31 depicts a side planar view of another exemplary embodiment of a bender, shown in a partially closed position.
Figure 32:
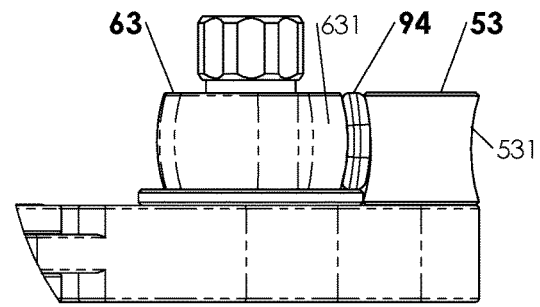
FIG. 32 is an enlarged view of area 32 in FIG. 31.
Figure 33:
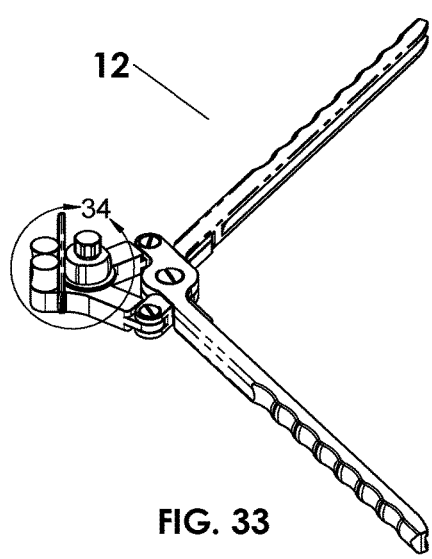
FIG. 33 depicts a top perspective view of the embodiment of FIG. 31, shown in a partially closed position.
Figure 34:
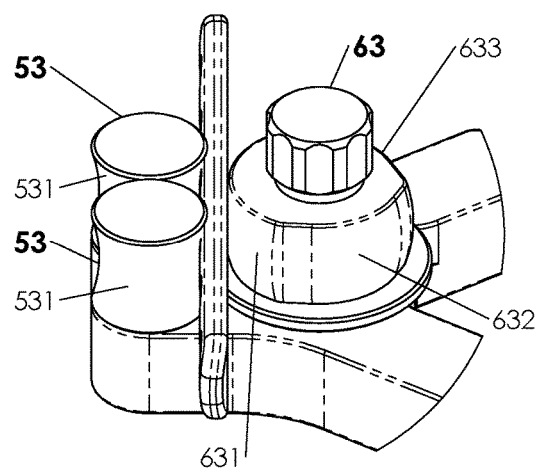
FIG. 34 is an enlarged partial top view of the area 34 shown in FIG. 33.

FIGS. 28-34 show another exemplary embodiment of a bender 12, where some of the items to be bent include bone plates having concave and/or convex outer surfaces (see curved/flat surfaces 941 and 942 of FIG. 30). When the plate to be bent may incorporate these types of surfaces, the bending rollers surfaces 53 and/or cam surfaces 631, 632 and 633 may be provided (i.e., cast, machined and/or formed) to match or substantially conform to some or all of the concave and/or convex surfaces of the bone plate 94. Those skilled in the art will understand that the convex and concave surfaces could also be switched so that the concave surface is on the top of the plate and the convex surface on the bottom; or both surfaces can be concave or convex with the bending rollers and cam machined to match.

FIGS. 35-37 depict other views of embodiment 11, where the items to be bent include bone plates or other items having flattened outer surfaces. In this embodiment, the bender can include a cam 62 and rollers 52 having corresponding flattened outer surfaces, and the cam can further include outer surfaces of varying radii, similar to the various cam surfaces previously described in conjunction with other embodiments.

Figure 41:
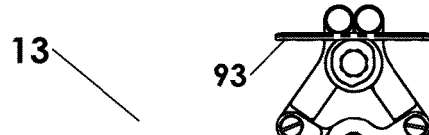
FIGS. 41 and 42 depict top and side planar views of another exemplary embodiment of a bender, shown in an open position.
Figure 42:
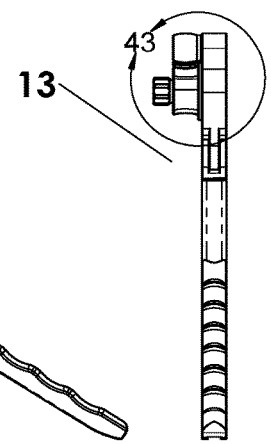
Figure 43:
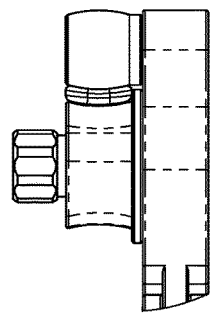
FIG. 43 is an enlarged partial side view of the area 43 shown in FIG. 42.

FIGS. 41-43 depict another exemplary embodiment of a bender 13, where some of the items to be bent include bone plates or other items having curved outer surfaces, where the items will desirably be bent away from the concave curvature of the plate. In this embodiment, the cam can include a concavely curved outer surface, with corresponding convexly curved rollers.

Figure 44:
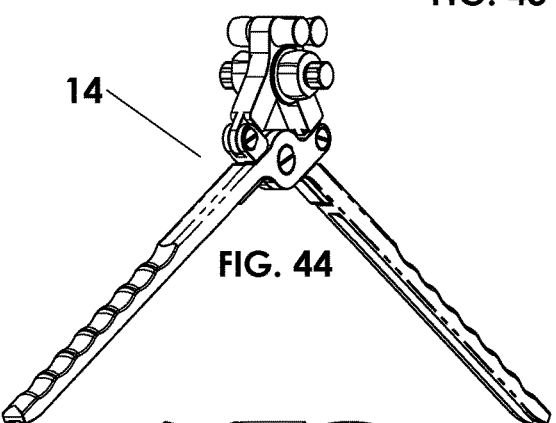
FIGS. 44 and 45 depict top and side planar views of another exemplary embodiment of a bender, shown in an open position.
Figure 45:
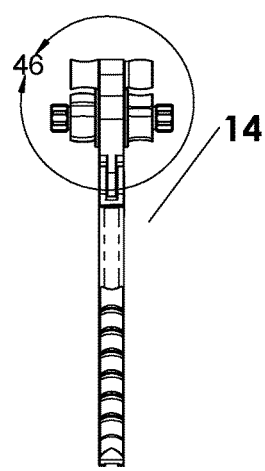
Figure 46:
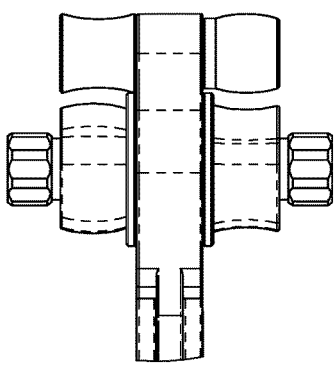
FIG. 46 is an enlarged partial side view of the area 46 shown in FIG. 45.
Figure 47:
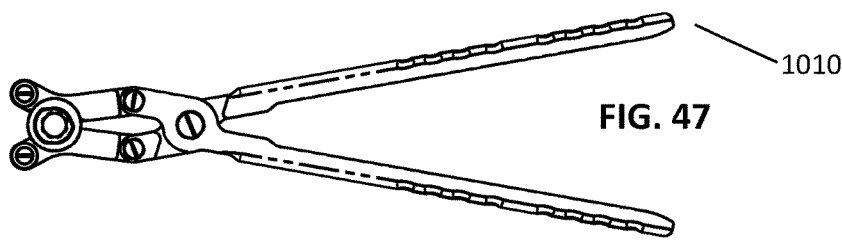
FIGS. 47-51 depict various views of another exemplary embodiment of a bender.
Figure 48:
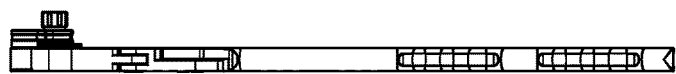
Figure 49:
Figure 50:
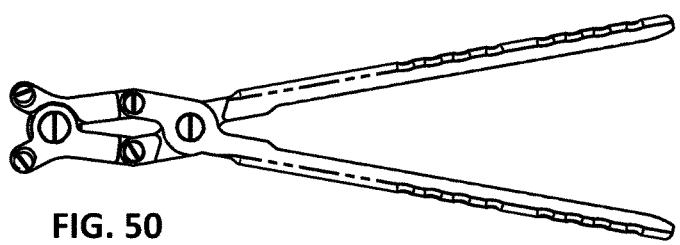
Figure 51:
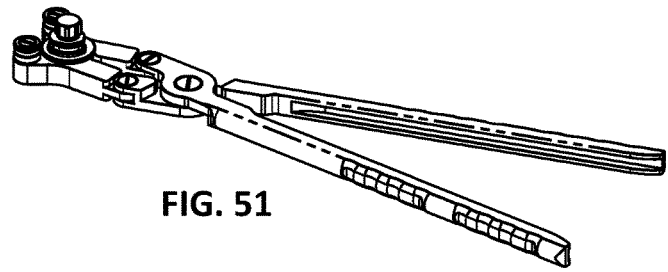

FIGS. 44-46 depict another exemplary embodiment of a bender 14, wherein the bender incorporates two different pairs of rollers and cams on opposing faces of the tool. This arrangement would be particularly useful where a surgeon wishes to bend different shaped objects during a single surgical procedure (i.e., one roller/cam set incorporates curved surfaces and the opposing roller/cam set incorporates flattened surfaces), where a single bending tool is desirous for multiple surgeries, and/or where a surgeon may have over-bent an item and wishes to bend that item in an opposing direction. If desired, the opposing cams may form a single component (i.e., the cams rotate together), or the cams may rotate independently from one another. Alternatively, the cam on a first side might incorporate cam surfaces having a first range of radii, and the cam on the opposing side might incorporate cam surfaces having a second range of radii, the first and second range of radii not overlapping and/or overlapping to some degree to each other (i.e., to accommodate items to be bent of a wide range of sizes using a single bending tool)

FIGS. 47-52 depict another exemplary embodiment of a bender 1010. Because many of the components of this embodiment are similar in many respects to the bender of FIG. 2, like numerals are used to denote similar components. In this embodiment, the bender 1010 includes a plurality of arms 20a, 21a, 30a and 40a. While the first set of arms 20a and 21a are shown as identical or "mirror-image" components in the present embodiment, but those of ordinary skill should realize that the two arms could contain features that make them unique without limiting the intent of the invention.

As depicted, arms 20a and 21a are pivotally joined in a pivot diameter, and desirably incorporate travel limiting surface features 203a that desirably stop the pivoting movement of the handles coming together when the surfaces 203a contact each other in a closing direction. In an opening direction, various surfaces (similar to those previously described) will desirably stop the pivoting movement of the arms at a maximum opening distance.

In this embodiment, the bender 1010 includes lightening grooves 206a, which are incorporated to desirably reduce the weight of the arms. One or more arms could further include replaceable, or permanently bonded, grip inserts 207a, which can fit into corresponding depressions or slots 208a formed in the arms—with the insert secured by a taper or friction fit, or by adhesives, etc. The use of replaceable grip inserts desirably facilitates the replacement of worn grip surfaces, and may also allow a surgeon to alter the grip surface to a desired surface texture, including textured surfaces of a desired shape and/or roughness as well as surfaces unlikely to damage surgical gloves, etc. Various exemplary inserts could include textured metal, ceramics, plastics and/or silicone materials, among others.

Figure 52:
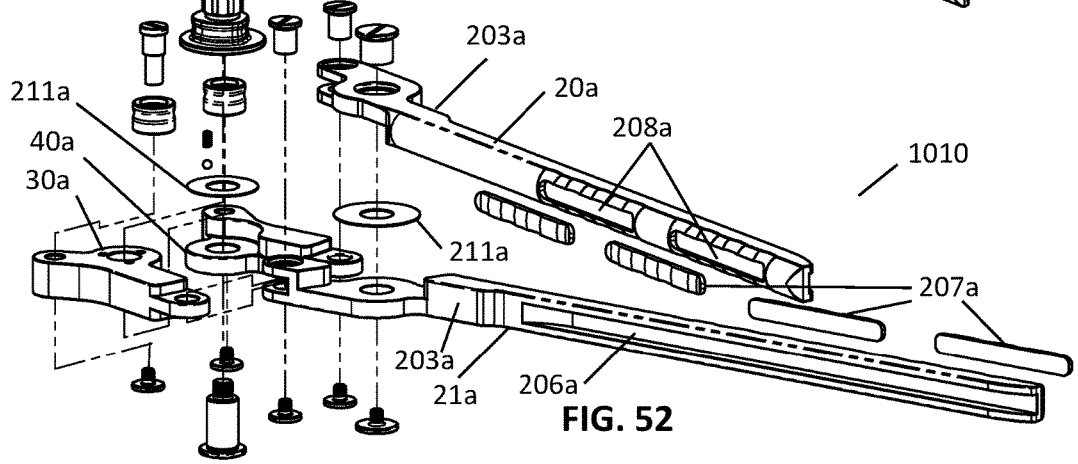
FIG. 52 depicts an exploded perspective view of the embodiment of FIG. 47.
Figure 59:
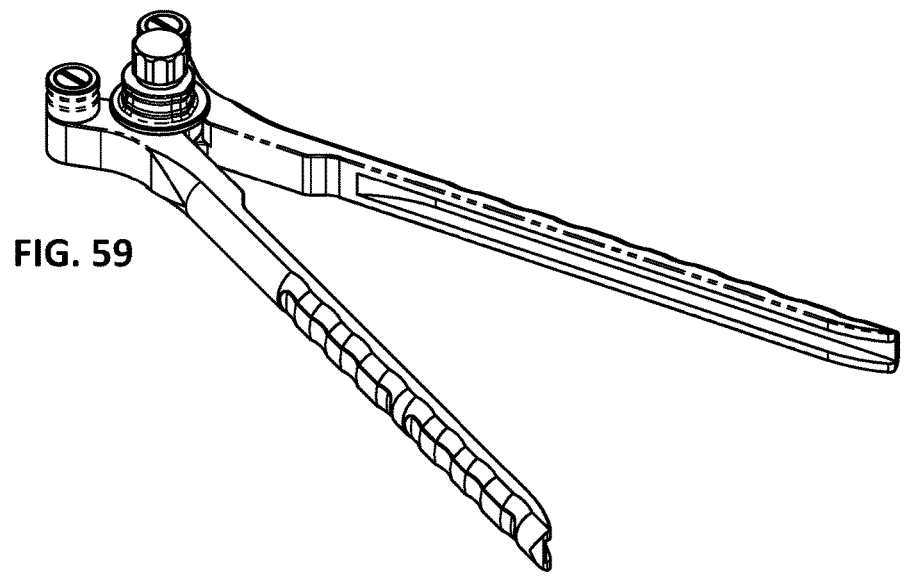
FIG. 59 depicts a perspective view of one exemplary embodiment of a single fulcrum bender.
Figure 60:
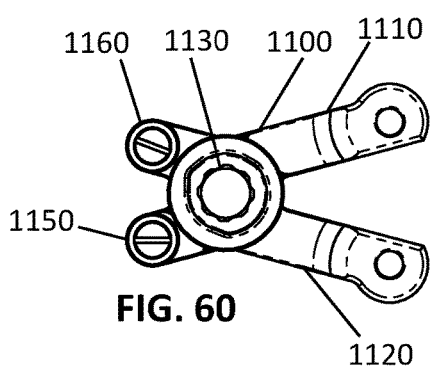
FIGS. 60-64 depict various views of one exemplary embodiment of a modular fulcrum augment to a bender.
Figure 61:
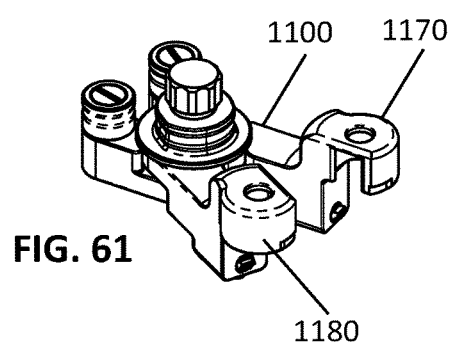
Figure 62:
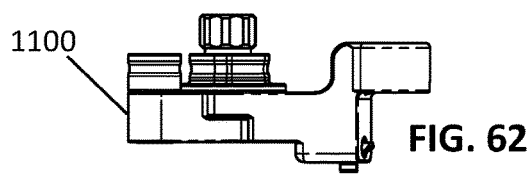
Figure 63:
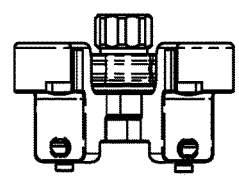
Figure 64:
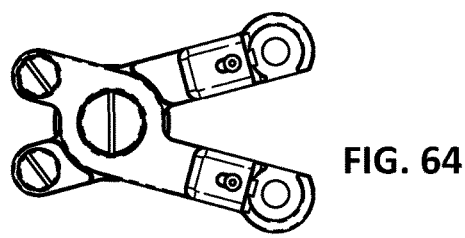

One or more thrust washers and/or spring friction washers 211a might be incorporated into the bender 1010 between arms 20a and 21a, and arms 30a and 31a of FIG. 52, which desirably assist with maintaining the bender 1010 in a desired resting position (i.e., fully and/or partially open and/or closed, or various positions there between) absent user input force. If desired, similar washers can be utilized to reduce the amount of friction between the surfaces 20a and 21a, and between surfaces 30a and 31a.

Alternative Configurations

The various components described herein may be formed in a variety of shapes, sizes and/or configurations. For example, the various embodiments disclosed herein may be formed in a variety of shapes and configurations, which will desirably facilitate the use of the bender. Similarly, the various features described herein could include features that are unique to a specific implant without departing from the sprit or essential character of the invention.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing from the spirit or essential characteristics thereof. The foregoing embodiments are therefore to be considered in all respects illustrative rather than limiting on the invention described herein. The scope of the invention is thus intended to include all changes that come within the meaning and range of equivalency of the descriptions provided herein.

Many of the aspects and advantages of the present invention may be more clearly understood and appreciated by reference to the accompanying drawings. The accompanying drawings are incorporated herein and form a part of the specification, illustrating embodiments of the present invention and together with the description, disclose the principles of the invention.

Although the foregoing inventions have been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein.

What is claimed is:

1. An instrument for bending an item comprising:
    a first pair of pivotable engaged opposing lever arms;
    a first pivot interconnecting the first pair of lever arms, the first pivot dividing each of the first pair of lever arms into a handle portion for opening and closing the first pair of lever arms and a second portion operable by the handle portion, the handle portion including a length A and the second portion including a length B, wherein length A is greater than length B;
    a second pair of pivotable engaged opposing lever arms;
    a second pivot interconnecting the second pair of lever arms, the second pivot dividing each of the second pair of lever arms into a driving portion for opening and closing the second pair of lever arms and a bending portion operable by the driving portion, the driving portion including a length C and the bending portion including a length D, wherein length C is greater than length D;
    a proximal portion of each driving portion pivotally mounted to a distal portion of each second portion, wherein opening and closing of the first pair of lever arms actuates closing and opening of the second pair of lever arms;
    a first three post bending assembly mounted on the bending portion, the first three post bending assembly including a first center post mounted on said second pivot and having a peripheral bending surface for contacting a portion of the item, and a pair of outer posts, one of each pair of outer posts mounted on each of the second pair of lever arms and pivotable thereon, the first center post being positioned relative to the pair of outer posts so as to define a channel there between for receiving the item when the first pair of lever arms are open, the outer posts forcing said item to bend about the peripheral bending surface when the first pair of lever arms are forcibly closed, said peripheral bending surface determining in part the shape of said bend; and
    a second three post bending assembly mounted on the bending portion, the second three post bending assembly including a second center post mounted on said second pivot on an opposing side from the first center post, the second center post having a second peripheral bending surface for contacting a portion of the item, and a second pair of outer posts, one of each second pair of outer posts mounted on each of the second pair of lever arms and pivotable thereon, the second center post being positioned relative to the second pair of outer posts so as to define a second channel there between for receiving the item when the first pair of lever arms are open, the second pair of outer posts forcing said item to bend about the second peripheral bending surface when the first pair of lever arms are forcibly closed, said second peripheral bending surface determining in part the shape of said bend.

2. The instrument of claim 1, wherein length B is equal to length C.

3. The instrument of claim 1, wherein length B is greater than length C.

4. The instrument of claim 1, wherein length B is less than length C.

5. The instrument of claim 1, wherein the peripheral bending surface for contacting a portion of the item comprises a plurality of selectively lockable bending surfaces circumferentially spaced around the peripheral surface of the single center post for contacting a portion of the item.

6. The instrument of claim 5, wherein the center post is mounted on the second pivot and is rotatable and lockable to one of the second pair of lever arms with said bending surfaces in a preselected position.

7. The instrument of claim 1, wherein each of the first pair of pivotable engaged opposing lever arms are identical in shape.

8. The instrument of claim 1, wherein each of the second pair of pivotable engaged opposing lever arms are identical in shape.

9. The instrument of claim 1, wherein at least a portion of each handle portion includes a slot for accommodating a removable grip insert.

10. The instrument of claim 1, wherein the handle portions include a positive stop that prevents at least a portion of the handle portions from contacting each other when the first pair of pivotable engaged opposing lever arms are closed.

11. A multiple fulcrum bender comprising:
    a first handle arm and a second handle arm coupled to a first pivot point;
    a third handle arm pivotally connected to the first handle arm at a second pivot point, the second pivot point located proximate to a distal end of the first handle;

a fourth handle arm pivotally connected to the second handle arm at a third pivot point, the third pivot point located proximate to a distal end of the second handle;

the third handle arm coupled to the fourth handle arm at a fourth pivot point;

the first pivot point located between a proximal end of the first handle and the second pivot point, the first pivot point further located between a proximal end of the second handle and the third pivot point;

a single center post mounted at the fourth pivot point and having a peripheral bending surface for contacting a portion of an item to be bent, a first outer post pivotally mounted on a distal portion of the third handle;

a second outer post pivotally mounted on a distal portion of the fourth handle;

the single center post and first and second outer posts comprising a three post bending assembly, the center post being positioned relative to the first and second pair of outer posts so as to define a channel there between for receiving the item when the first and second handle arms are in an open position, the first and second outer posts forcing said item to bend about the peripheral bending surface when the first and second handle arms are forcibly closed, the peripheral bending surface determining in part the shape of the bend.

12. The multiple fulcrum bender of claim 11, wherein the first handle arm and the second handle arm are substantially identical in shape and size.

13. The multiple fulcrum bender of claim 11, wherein the third handle arm and the fourth handle arm are substantially identical in shape and size.

14. The instrument of claim 11, wherein at least a portion of the first and second handle arms includes a slot for accommodating a removable grip insert.

15. The multiple fulcrum bender of claim 11, wherein the peripheral bending surface for contacting the portion of the item to be bent comprises a plurality of selectively lockable bending surfaces circumferentially spaced around the peripheral surface of the single center post for contacting a portion of the item.

16. The multiple fulcrum bender of claim 11, further comprising a second three post bending assembly mounted on the third and fourth handle arms, the second three post bending assembly including a second center post mounted on said fourth pivot point on an opposing side from the single center post, the second center post having a second peripheral bending surface for contacting a portion of the item to be bent, and a second pair of outer posts, one of each second pair of outer posts mounted on each of the third and fourth handles and pivotable thereon, the second center post being positioned relative to the second pair of outer posts so as to define a second channel there between for receiving the item to be bent when the first and second handle arms are in the open position, the second pair of outer posts forcing said item to be bent to bend about the second peripheral bending surface when the first and second handle arms are forcibly closed, said second peripheral bending surface determining in part the shape of said bend.

17. The multiple fulcrum bender of claim 15, wherein at least two of the plurality of selectively lockable bending surfaces have different radii.

18. The multiple fulcrum bender of claim 15, wherein at least two of the plurality of selectively lockable bending surfaces have different surface shapes.

* * * * *